(12) United States Patent
Lima et al.

(10) Patent No.: US 11,986,408 B2
(45) Date of Patent: May 21, 2024

(54) STENT WITH MID-CROWNS

(71) Applicant: Medtronic Vascular, Inc., Santa Rosa, CA (US)

(72) Inventors: Carlos Lima, Corte Madera, CA (US); Richard Bliss, Cloverdale, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 17/382,005

(22) Filed: Jul. 21, 2021

(65) Prior Publication Data
US 2022/0023075 A1 Jan. 27, 2022

Related U.S. Application Data

(60) Provisional application No. 63/056,157, filed on Jul. 24, 2020.

(51) Int. Cl.
*A61F 2/915* (2013.01)
*A61F 2/88* (2006.01)

(52) U.S. Cl.
CPC ............... *A61F 2/915* (2013.01); *A61F 2/88* (2013.01); *A61F 2002/9155* (2013.01); *A61F 2230/0091* (2013.01)

(58) Field of Classification Search
CPC .... A61F 2/915; A61F 2/82; A61F 2/88; A61F 2/90; A61F 2002/9155; A61F 2002/91525; A61F 2230/0091
See application file for complete search history.

(56) References Cited

U.S. PATENT DOCUMENTS 5,716,396 A    2/1998  Williams, Jr.
5,948,016 A    9/1999  Jang
             (Continued)

FOREIGN PATENT DOCUMENTS

EP    1245203 A2   10/2002
FR    2760351 A1    9/1998
             (Continued)

OTHER PUBLICATIONS

International Search Report and Written Opinion issued in International Application No. PCT/US2021/042907 dated Oct. 28, 2021.
(Continued)

*Primary Examiner* — Dinah Baria
(74) *Attorney, Agent, or Firm* — Medler Ferro Woodhouse & Mills PLLC

(57) ABSTRACT

A continuous wire stent includes a wire bent into a waveform and spirally wrapped into a helix having a plurality of bands that form a hollow cylindrical shape. The waveform includes a plurality of waves, each wave including a first outer crown including a first intrados, a second outer crown including a second intrados facing the first intrados, a first mid-crown disposed between the first outer crown and the second outer crown, a second mid-crown disposed between the second outer crown and an outer crown of a next wave of the waveform, a first strut connecting the first outer crown to the first mid-crown, a second strut connecting the first mid-crown to the second outer crown, a third strut connecting the second outer crown to the second mid-crown, and a fourth strut connecting the second mid-crown to the outer crown in the next wave of the waveform.

8 Claims, 10 Drawing Sheets

(56) References Cited

U.S. PATENT DOCUMENTS

| | | |
|---|---|---|
| 6,200,334 B1 | 3/2001 | Jang |
| 6,235,053 B1 | 3/2001 | Jang |
| 6,398,805 B1 | 6/2002 | Alt |
| 6,491,718 B1 | 12/2002 | Ahmad |
| 6,602,285 B1 | 8/2003 | Von Oepen et al. |
| 6,682,554 B2 | 1/2004 | Von Oepen et al. |
| 6,755,856 B2 | 6/2004 | Fierens et al. |
| 6,776,794 B1 | 8/2004 | Hong et al. |
| 6,814,749 B2 | 11/2004 | Cox et al. |
| 6,821,292 B2 | 11/2004 | Pazienza et al. |
| 6,881,222 B2 | 4/2005 | White et al. |
| 6,939,373 B2 | 9/2005 | Gomez et al. |
| 7,128,756 B2 | 10/2006 | Lowe et al. |
| 7,179,285 B2 | 2/2007 | Ikeuchi et al. |
| 7,329,277 B2 | 2/2008 | Addonizio et al. |
| 7,404,823 B2 | 7/2008 | Gregorich et al. |
| 7,491,227 B2 | 2/2009 | Yang et al. |
| 7,618,445 B2 | 11/2009 | Moriuchi et al. |
| 7,625,401 B2 | 12/2009 | Clifford et al. |
| 7,645,297 B2 | 1/2010 | Nissl |
| 7,651,524 B2 | 1/2010 | Moriuchi et al. |
| 7,691,142 B2 | 4/2010 | Nissl |
| 7,803,179 B2 | 9/2010 | Denison |
| 7,879,084 B2 | 2/2011 | Goto |
| 7,887,578 B2 | 2/2011 | Schneider |
| 7,972,373 B2 | 7/2011 | Contiliano et al. |
| 7,981,149 B2 | 7/2011 | Contiliano et al. |
| 7,985,251 B2 | 7/2011 | Ikeuchi et al. |
| 8,016,876 B2 | 9/2011 | Gregorich et al. |
| 8,043,358 B2 | 10/2011 | Weber et al. |
| 8,048,142 B2 | 11/2011 | Venturelli |
| 8,070,792 B2 | 12/2011 | Gregorich et al. |
| 8,105,373 B2 | 1/2012 | Girton et al. |
| 8,109,991 B2 | 2/2012 | Clifford et al. |
| 8,147,538 B2 | 4/2012 | Brown et al. |
| 8,157,858 B2 | 4/2012 | Goto |
| 8,287,587 B2 | 10/2012 | Moriuchi |
| 8,303,645 B2 | 11/2012 | Von Oepen et al. |
| 8,323,331 B2 | 12/2012 | Dreher |
| 8,337,544 B2 | 12/2012 | Osman et al. |
| 8,348,991 B2 | 1/2013 | Weber et al. |
| 8,430,924 B2 | 4/2013 | Ehr et al. |
| 8,449,596 B2 | 5/2013 | Goto |
| 8,523,935 B2 | 9/2013 | Fliedner |
| 8,523,938 B2 | 9/2013 | Takeuchi et al. |
| 8,556,959 B2 | 10/2013 | Goto |
| 8,562,665 B2 | 10/2013 | Jang |
| 8,585,752 B2 | 11/2013 | Sudo et al. |
| 8,608,794 B2 | 12/2013 | Girton et al. |
| 8,652,196 B2 | 2/2014 | Nissl |
| 8,721,705 B2 | 5/2014 | White et al. |
| 8,728,146 B2 | 5/2014 | Gregorich et al. |
| 8,740,967 B2 | 6/2014 | Mitsudo et al. |
| 8,882,824 B2 | 11/2014 | Kim et al. |
| 8,916,226 B2 | 12/2014 | Mauch et al. |
| 8,920,488 B2 | 12/2014 | Bregulla |
| 8,986,366 B2 | 3/2015 | Girton et al. |
| 9,095,459 B2 | 8/2015 | Maruyama et al. |
| 9,265,636 B2 | 2/2016 | Chanduszko |
| 9,445,927 B2 | 9/2016 | Lee et al. |
| 9,526,643 B2 | 12/2016 | Goto |
| 9,603,732 B2 | 3/2017 | Ma et al. |
| 9,801,743 B2 | 10/2017 | Kreidler et al. |
| 9,827,120 B2 | 11/2017 | Gregorich et al. |
| 10,327,926 B2 | 6/2019 | Lee et al. |
| 10,420,637 B2 | 9/2019 | Fierens et al. |
| 10,420,660 B2 | 9/2019 | Shobayashi |
| 10,603,194 B2 | 3/2020 | Zhao et al. |
| 2001/0047200 A1 | 11/2001 | White et al. |
| 2003/0014102 A1 | 1/2003 | Hong et al. |
| 2003/0144731 A1 | 7/2003 | Wolinsky et al. |
| 2006/0004436 A1 | 1/2006 | Amarant et al. |
| 2006/0060266 A1 | 3/2006 | Bales et al. |
| 2006/0100690 A1 | 5/2006 | Venturelli |
| 2007/0016283 A1 | 1/2007 | Greenhalgh et al. |
| 2007/0078511 A1 | 4/2007 | Ehr et al. |
| 2007/0208411 A1 | 9/2007 | Meyer et al. |
| 2008/0281407 A1 | 11/2008 | Addonizio et al. |
| 2008/0294267 A1 | 11/2008 | Chanduszko |
| 2009/0093869 A1 | 4/2009 | Cunniffe et al. |
| 2009/0105809 A1 | 4/2009 | Lee et al. |
| 2010/0094405 A1 | 4/2010 | Cottone |
| 2010/0131044 A1 | 5/2010 | Patel |
| 2010/0204780 A1 | 8/2010 | Fliedner et al. |
| 2011/0054592 A1 | 3/2011 | Fliedner |
| 2011/0166641 A1 | 7/2011 | Bales, Jr. et al. |
| 2011/0218614 A1* | 9/2011 | Lam .................. A61F 2/90 623/1.15 |
| 2013/0282107 A1 | 10/2013 | Baldwin et al. |
| 2013/0317595 A1 | 11/2013 | Obradovic et al. |
| 2013/0345790 A1 | 12/2013 | Cottone |
| 2016/0206451 A1 | 7/2016 | Maruyama |
| 2018/0360628 A1 | 12/2018 | Yan et al. |
| 2019/0254847 A1 | 8/2019 | Lee et al. |

FOREIGN PATENT DOCUMENTS

| | | |
|---|---|---|
| WO | 2011/034795 A1 | 3/2011 |
| WO | 2012/096716 A2 | 7/2012 |
| WO | 2017/168196 A1 | 10/2017 |

OTHER PUBLICATIONS

International Search Report and Written Opinion issued in International Application No. PCT/US2021/042918 dated Oct. 29, 2021.

* cited by examiner

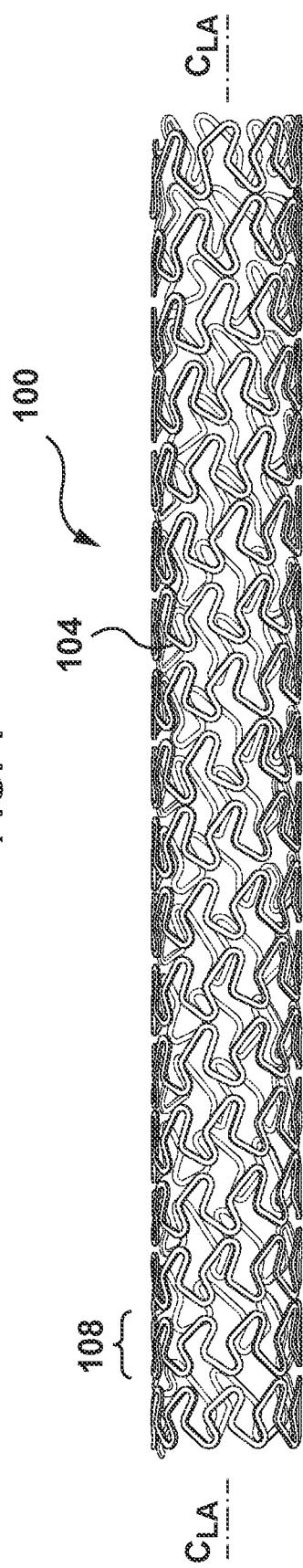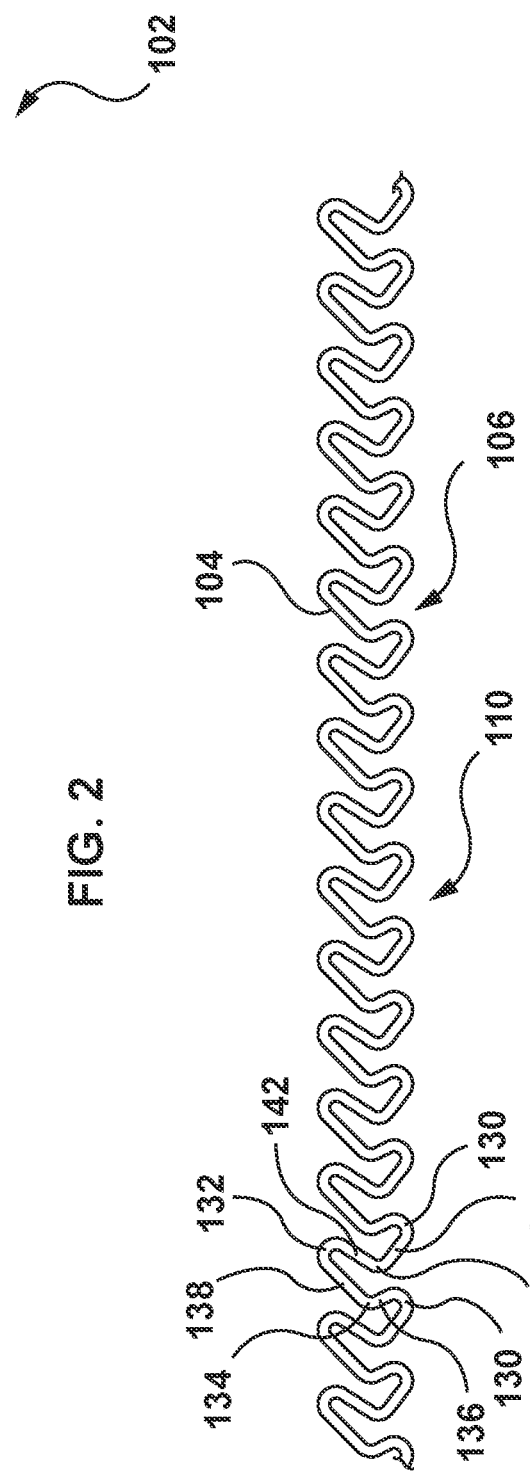

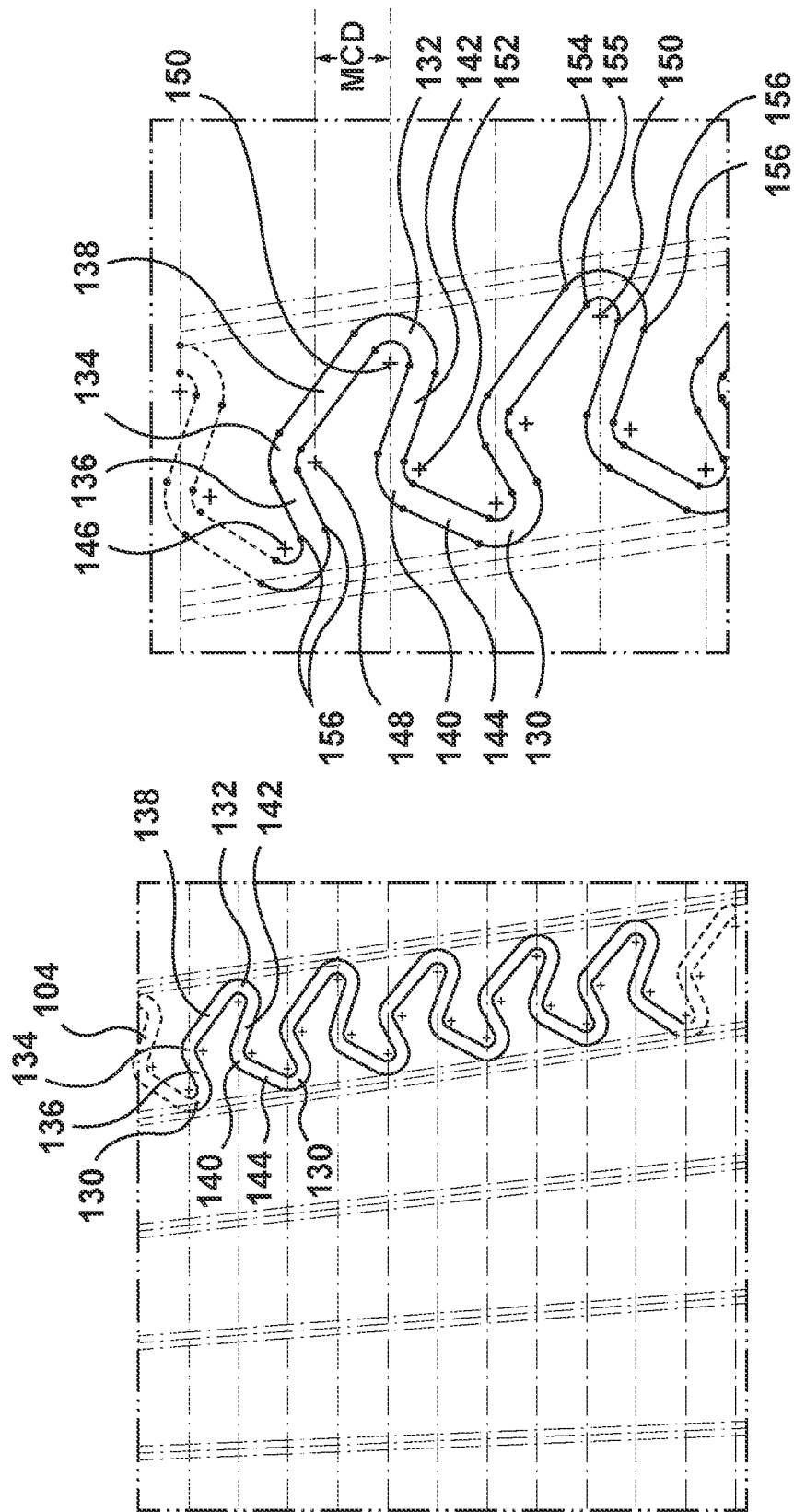

STENT WITH MID-CROWNS

CROSS-REFERENCE TO RELATED APPLICATIONS

This application claims benefit of the filing date of U.S. Provisional Application No. 63/056,157, filed Jul. 24, 2020, the contents of which are incorporated by reference herein in their entirety.

FIELD OF THE INVENTION

This invention generally relates to endoluminal prostheses or stents. More specifically, the invention relates to endoluminal prostheses or stents formed using a continuous wire.

BACKGROUND OF THE INVENTION

A stent is a type of endoluminal prosthesis. Stents are generally tubular open-ended structures providing support for damaged, collapsing, or occluded blood vessels. They are radially expandable from a radially compressed configuration for delivery to the affected vessel site to a radially expanded configuration when deployed at the affected vessel treatment site, with the radially expanded configuration having a larger diameter than the radially compressed configuration. Stents are generally inserted in the radially compressed configuration and expanded to the radially expanded configuration either through a self-expanding mechanism, or through the use of a balloon catheter.

BRIEF SUMMARY OF THE INVENTION

The design of a stent must balance several characteristics. For example, and not by way of limitation, characteristics such as force distortion, radial strength, overexpansion, crossing profile, flexibility, strut lift, retention, metal to artery ratio, drug load, and retention are some of the many characteristics used to drive optimization and design decisions. For example, using a thinner profile wire while keeping other variables the same for a given design, the radial strength of the stent decreases and risk of strut lifting and longitudinal distortion increase. If the thinner profile wire is paired with a decrease in strut lengths to maintain a similar radial strength, then the ability of the struts and crowns to open (referred to as overexpansion) is compromised.

Accordingly, there is a need for an improved continuous wire stent design that enables improved characteristics of the stent.

Embodiments hereof are directed to a continuous wire stent including a radially compressed configuration and a radially expanded configuration. In the radially compressed configuration, the continuous wire stent includes a wire bent into a waveform and spirally wrapped into a helix having a plurality of bands that form a hollow cylindrical shape of the overall stent. At least a portion of the helix includes a plurality of repeating body units including a plurality of waves. Each wave of the plurality of waves may include a first outer crown including a first intrados, a second outer crown including a second intrados facing the first intrados, a first mid-crown disposed between the first outer crown and the second outer crown, a second mid-crown disposed between the second outer crown and an outer crown of a next wave of the waveform, a first strut connecting the first outer crown to the first mid-crown, a second strut connecting the first mid-crown to the second outer crown, a third strut connecting the second outer crown to the second mid-crown, and a fourth strut connecting the second mid-crown to the outer crown in the next wave of the waveform.

Embodiments hereof are also directed to a continuous wire stent according to any of the embodiments herein, wherein the waves include a mid-crown wavelength distance in the range of greater than zero (0) to a distance where the mid crown is in contact with the adjacent crown above it.

Embodiments hereof are also directed to a continuous wire stent according to any of the embodiments herein, wherein the plurality of repeating body units are disposed in a central portion of the continuous wire stent.

Embodiments hereof are also directed to a continuous wire stent according any of the embodiments herein, wherein the helix in the central portion is wrapped at non-perpendicular angle with respect to a central longitudinal axis of the continuous wire stent. In embodiments, the non-perpendicular angle is between 60 and 85 degrees. In other embodiments, the non-perpendicular angle is between 70 and 85 degrees.

Embodiments hereof are also directed to a continuous wire stent according to any of the embodiments herein, wherein the continuous wire stent further includes a first end portion disposed to a first side of the central portion and a second end portion disposed to a second side of the central portion opposite the first end portion, wherein the first end portion and the second end portion are configured such that a first end of the continuous wire stent and a second end of the continuous wire stent are substantially orthogonal to a central longitudinal axis of the continuous wire stent. Embodiments hereof are also directed to a continuous wire stent according to any of the embodiments above, wherein the helix in the central portion is wrapped at a first angle with respect to a central longitudinal axis of the continuous wire stent, and wherein the helix in the first end portion is wrapped at a second angle with respect to the central longitudinal axis of the continuous wire stent, the second angle being different than the first angle.

Embodiments hereof are also directed to a continuous wire stent according to any of the embodiments herein, further including connections between adjacent bands of the helix, wherein each repeating body unit is defined between adjacent connections along the helix.

Embodiments hereof are also directed to a continuous wire stent including a radially compressed configuration and a radially expanded configuration. In the radially compressed configuration, the continuous wire stent includes a wire bent into a waveform and spirally wrapped into a helix having a plurality of bands that form a hollow cylindrical shape. At least a portion helix includes a plurality of repeating body units including a plurality of waves including a first outer crown including a first intrados, a second outer crown including a second intrados facing the first intrados, a first mid-crown disposed between the first outer crown and a second mid-crown, the second mid-crown being disposed between the first mid-crown and the second outer crown, a first strut connecting the first outer crown to the first mid-crown, a second strut connecting the first mid-crown to the second mid-crown, a third strut connecting the second mid-crown to the second outer crown, a third mid-crown is disposed between the second outer crown and a fourth mid-crown, the fourth mid-crown being disposed between the third mid-crown and an outer crown in a next wave of the waveform, a fourth strut connecting the second outer crown to the third mid-crown, a fifth strut connecting the third mid-crown to the fourth mid-crown, and a sixth strut connecting fourth mid-crown to the outer crown in the next wave of the waveform.

Embodiments hereof are also directed to a continuous wire stent according any of the embodiments herein, wherein the helix in the central portion is wrapped at non-perpendicular angle with respect to a central longitudinal axis of the continuous wire stent. In embodiments, the non-perpendicular angle is between 60 and 85 degrees. In other embodiments, the non-perpendicular angle is between 70 and 85 degrees.

Embodiments hereof are also directed to a continuous wire stent according to any of the embodiments herein, wherein the first outer crown includes a first outer crown center, the second outer crown includes a second outer crown center, the first mid-crown includes a first mid-crown center, the second mid-crown includes a second mid-crown center, the third mid-crown includes third mid-crown center, the fourth mid-crown includes a fourth mid-crown center, and the outer crown in the next wave of the waveform includes a next outer crown center.

Embodiments hereof are also directed to a continuous wire stent according to any of the embodiments herein, wherein in the radially compressed configuration, the second outer crown center, the third mid-crown center, the fourth mid-crown center, and the next outer crown center are co-linear on a line that is parallel to a central longitudinal axis of the continuous wire stent.

Embodiments hereof are also directed to a continuous wire stent according to any of the embodiments herein, wherein in the radially compressed configuration, the first outer crown center, the fourth mid-crown center, the third mid-crown center, and the second outer crown center are co-linear on a line that is parallel to a central longitudinal axis of the continuous wire stent.

Embodiments hereof are also directed to a continuous wire stent according to any of the embodiments herein, wherein in the radially compressed configuration, the first outer crown center, the first mid-crown center, the second mid-crown center, and the second outer crown center are co-linear on a line that is parallel to a central longitudinal axis of the continuous wire stent.

Embodiments hereof are also directed to a continuous wire stent according to any of the embodiments herein, wherein the third mid-crown center and the fourth mid-crown center are co-linear on a line that is parallel to the central longitudinal axis of the continuous wire stent.

Embodiments hereof are also directed to a continuous wire stent according to any of the embodiments herein, wherein the plurality of repeating body units are disposed in a central portion of the continuous wire stent.

Embodiments hereof are also directed to a continuous wire stent of according to any of the embodiments herein, wherein the continuous wire stent further includes a first end portion disposed to a first side of the central portion and a second end portion disposed to a second side of the central portion opposite the first end portion, wherein the first end portion and the second end portion are configured such that a first end of the continuous wire stent and a second end of the continuous wire stent are substantially orthogonal to a central longitudinal axis of the continuous wire stent.

Embodiments hereof are also directed to a continuous wire stent of according to any of the embodiments herein, wherein the helix in the central portion is wrapped at a first helical angle with respect to a central longitudinal axis of the continuous wire stent, and wherein the helix in the first end portion is wrapped at a second helical angle with respect to the central longitudinal axis of the continuous wire stent, the second helical angle being different than the first helical angle.

Embodiments hereof are also directed to a continuous wire stent according to any of the embodiments herein, wherein the continuous wire stent further includes connections between adjacent bands of the helix, wherein the each repeating body unit is defined between adjacent connections along the helix.

Embodiments hereof are also directed to a stent including a radially compressed configuration and a radially expanded configuration. The stent in the radially compressed configuration includes a central portion including a plurality of bands disposed adjacent to each other, the plurality of bands including a waveform including a plurality of waves. The wave includes a first outer crown including a first intrados, a second outer crown including a second intrados facing the first intrados, a first mid-crown disposed between the first outer crown and the second outer crown, a second mid-crown disposed between the second outer crown and an outer crown of a next wave of the waveform, a first strut connecting the first outer crown to the first mid-crown, a second strut connecting the first mid-crown to the second outer crown, a third strut connecting the second outer crown to the second mid-crown, and a fourth strut connecting the second mid-crown to the outer crown in the next wave of the waveform. Each of the plurality of bands in the central portion are disposed at a non-perpendicular angle with respect to a central longitudinal axis of the stent.

Embodiments hereof are also directed to a stent according the embodiments above, wherein the non-perpendicular angle is between 60 and 85 degrees. In other embodiments, the non-perpendicular angle is between 70 and 85 degrees.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a perspective view of a continuous wire stent in a radially compressed configuration according to an embodiment hereof.

FIG. 2 is a perspective view of the continuous wire stent of FIG. 1 in a radially expanded configuration.

FIG. 3 illustrates a portion of a wire bent into a waveform.

FIG. 5 is an enlarged view of a portion of the continuous wire stent of FIG. 4.

FIG. 6 is an enlarged view of a portion of the continuous wire stent of FIG. 4.

DETAILED DESCRIPTION OF THE INVENTION

Figure 4:
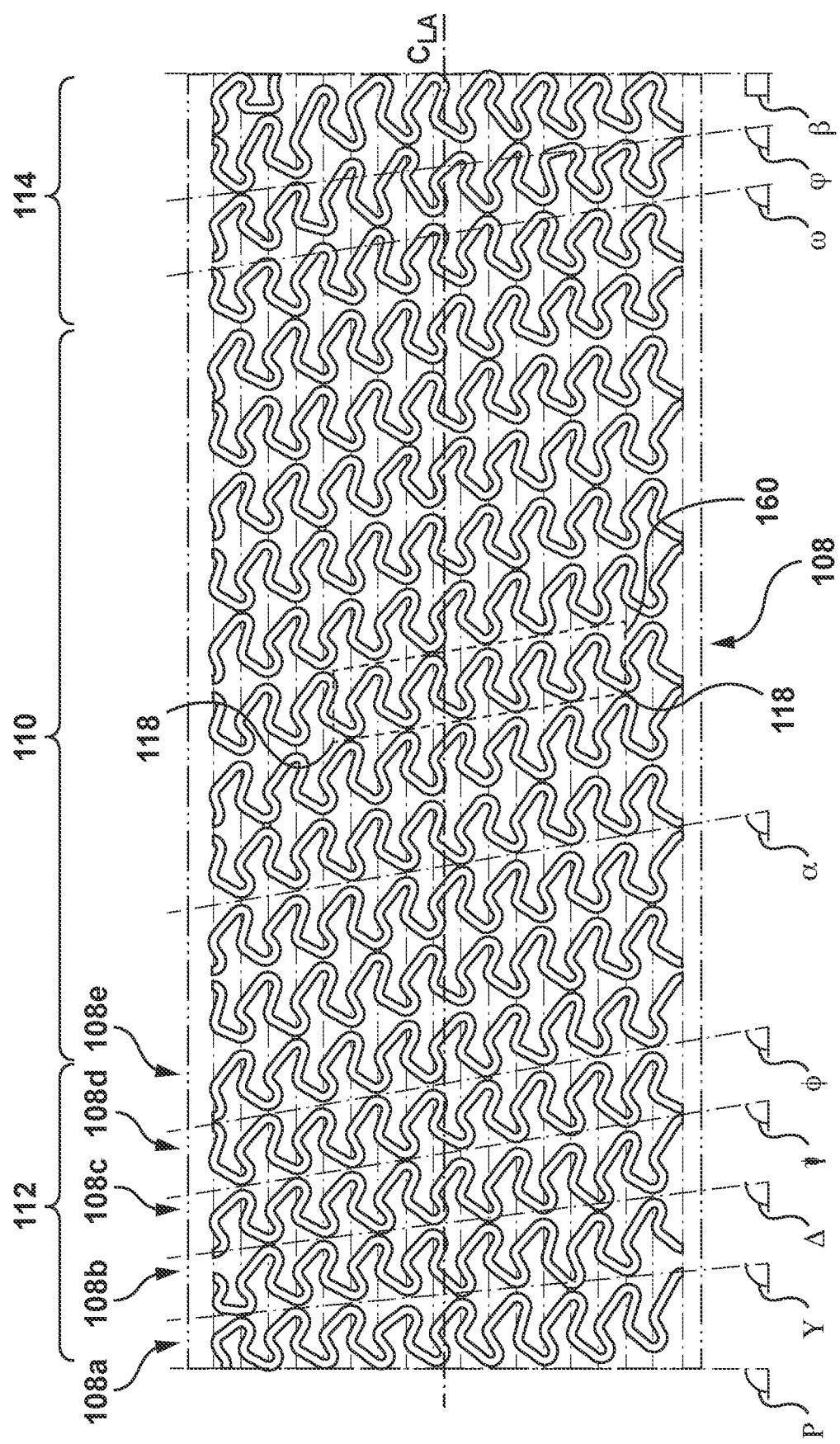
FIG. 4 is a flat layout view of the continuous wire stent of FIG. 1.

Specific embodiments of the present invention are now described with reference to the figures, wherein like reference numbers indicate identical or functionally similar elements.

The following detailed description is merely exemplary in nature and is not intended to limit the invention or the application and uses of the invention. Although the description of the invention is in the context of treatment of blood vessels, the invention may also be used in any other body passageways where it is deemed useful. Furthermore, there is no intention to be bound by any expressed or implied theory presented in the preceding technical field, background, brief summary or the following detailed description.

The term "continuous wire stent" as used herein means a stent form by from a wire that is bent into a waveform and helically wrapped around a central longitudinal axis to form a tube. Stents that are formed, e.g., by laser cutting a tube to removed portions such that the portions that are not removed from the stent are not "continuous wire stents".

As used herein the term "crown" is a turn or bend in wire.

As used herein the term "strut" is a generally straight portion of a wire connecting two crowns together.

FIG. 1 is a perspective view of a continuous wire stent 100 according to an embodiment hereof. The continuous wire stent 100 includes a radially compressed configuration for delivery to the affected site of a blood vessel, as shown in FIG. 1, and a radially expanded configuration when deployed, which is shown in FIG. 2. The continuous wire stent 100 is a generally tubular, open-ended structure having a first end 109 and a second end 111, and defines a lumen 102 therethrough. The continuous wire stent 100 may be self-expanding or balloon expandable. The continuous wire stent 100 is formed from a wire 104 formed into a waveform 106 and then helically wrapped (such as around a mandrel) to form the continuous wire stent 100. Other steps in processing the wire 104 and/or the continuous wire stent 100 may also be included. For example, and not by way of limitation, the wire 104 may be swaged prior to or after forming the wire 104 into the waveform 106. Swaging the wire 104 reduces the overall cross-section or diameter of the wire 104. Other steps such as connections between adjacent bands in the wrapped waveform, as explained in more detail below, polishing and other finishing steps may also be used in forming the continuous wire stent 104.

The wire 104 is a continuous element or strand that is bent into the waveform 106, as shown in FIG. 3, and is wrapped into a helix having a plurality of windings, turns, or bands 108 that form a hollow cylindrical shape of the overall continuous wire stent 100. In the embodiment shown in FIGS. 1-6, the continuous wire stent 100 includes nineteen bands 108. However, this is not limiting and the continuous wire stent 100 may include more or fewer bands 108. In the embodiment of FIGS. 1-6, the bands 108 form three portions of the continuous wire stent 100, a central portion 110, a first end portion 112 disposed to a first side of the central portion 110, and a second end portion 114 disposed to a second side of the central portion 110 opposite the first end portion 112.

The bands 108 are generally angled with respect to a central longitudinal axis CLA of the continuous wire stent 100 such that the bands or windings 108 are not perpendicular to the central longitudinal axis CLA.

In an embodiment, in order to the continuous wire stent 100 with ends that are substantially orthogonal to the central longitudinal axis CLA, the waveform 106 is wrapped around the central longitudinal axis CLA at different pitches. The term "substantially orthogonal" as used herein means within 2 degrees of orthogonal. The term "substantially orthogonal" as used herein also means that all of the crowns disposed at an end of the stent are aligned orthogonally, but one or two crowns are not aligned with the other crowns. As illustrated in FIG. 4, the waveform 106 is wrapped around the central longitudinal axis CLA at different pitches so that the waveform 106 generally defines a helical coil in the central portion 110 having a central helical or pitch angle $\alpha$, and also defines ends that are substantially square, orthogonal, or perpendicular with the central longitudinal axis CLA. As illustrated, the first end portion 112 includes a first band 108a that is wrapped about the central longitudinal axis CLA at a first angle $\beta$ of about 90° so that the continuous wire stent 100 has an end that is substantially square, orthogonal, or perpendicular to the central longitudinal axis CLA. In an embodiment, the first angle $\beta$ may be greater than 90°.

The first end portion 112 also includes a second band 108b that is a continuation of the waveform 106 from the first band 108a. The second band 108b is wrapped about the central longitudinal axis LA at a second pitch angle $\gamma$ that is less than 90° but greater than the central pitch angle $\alpha$. In the embodiment shown in FIGS. 1-5, third, fourth, and fifth bands 108c, 108d, 108e are also part of the first end portion 112, and may be configured to provide a more gradual transition between the first band 108a that is wrapped about the central longitudinal axis CLA at about 90° and the central pitch angle $\alpha$ of the central portion 110. In the illustrated embodiment, the third band 108c is wrapped about the central longitudinal axis LA at a third pitch angle $\Delta$, which is greater than the central pitch angle $\alpha$ but less than the second pitch angle $\gamma$. The fourth band 108d of the first end portion 112 is wrapped about the central longitudinal axis CLA at a fourth pitch angle $\psi$, which is greater than the central pitch angle $\alpha$ but less than the third pitch angle $\Delta$. The fifth band 108e is wrapped about the central longitudinal axis CLA at a fifth pitch angle $\o$, which is greater than the central pitch angle $\alpha$ but less than the fourth pitch angle $\psi$.

As also illustrated in FIG. 4, the second end portion 114 is not necessarily a mirror image of the first end portion 112. In the embodiment of FIGS. 1-5, the first end portion 112 includes a total of five bands 108a, 108b, 108c, 108d, 108e, while the second end portion 114 includes three bands 108p, 108q, 108r. The band 108r of the second end portion 114 adjacent the second end 111 of the continuous wire stent 100 has a pitch angle $\beta$ of about 90° so that the end of the second end 111 is substantially orthogonal to the central longitudinal axis CLA. In an embodiment, the band 108r of the second end portion 114 of the continuous wire stent 100 has a pitch angle that is greater than 90°. The next band 108q is wrapped about the central longitudinal axis CLA at a pitch angle $\varphi$, which is less than the angle $\beta$, but greater than the central pitch angle $\alpha$ of the central portion 110. The next band 108p is wrapped about the central longitudinal axis CLA at a pitch angle $\omega$, which is less than the pitch angle $\varphi$ of the band 108q, but greater than the central pitch angle $\alpha$ of the central portion 110.

More details regarding the first and second end portions 112, 114 can be found in U.S. Pat. No. 9,060,889, assigned to Medtronic Vascular, Inc., which is incorporated by reference herein in its entirety. Further, the first and second end portions 112, 114 are not limited to the embodiments described above. For example, and not by way of limitation, other embodiments for the end portions described in the '889 patent may be utilized with the waveform 106 described in more detail herein, or other end portions that would be apparent to those skilled in the art.

The waveform 106 shown in FIG. 3 is the waveform 106 for the central portion 110. The first and second end portions 112, 114 may include the same waveform except that certain struts of the waveform for the first and second end portions 112, 114 may be longer than other struts, as explained in the '889 patent. As best shown in FIGS. 3, 5, and 6, the waveform 106 generally includes a repeating series of a first outer bend or crown 130, a second outer bend or crown 132, a first mid-bend or mid-crown 134 disposed between the first outer crown 130 and the second outer crown 132, and a second mid-bend or mid-crown 140 disposed between the second outer crown 132 and the first outer crown 130 in the next wave of the waveform 106. The inner curve or intrados of the first outer crown 130 faces the inner curve or intrados of the second outer crown 132 such that the first outer crown 130 turns the wave towards the second outer crown 132 and the second outer crown 132 turns the wave towards the first outer crown 130. A first strut 136 connects the first outer crown 130 to the first mid-crown 134, a second strut 138 connects the first mid-crown 134 to the second outer crown 132, a third strut 142 connects the second outer crown 132 to the second mid-crown 140, and fourth strut 144 connects the second mid-crown 140 to the first outer crown 130 in the next wave of the waveform 106. Thus, a complete wave of the waveform 106 in a particular order starting from one of the first outer crowns 130 is the first outer crown 130, the first strut 136, the first mid-crown 134, the second strut 138, the second outer crown 132 turning the wave in a generally opposite direction, the third strut 142, the second mid-crown 140, and the fourth strut 144 connecting to another first crown 130 in the next wave of the waveform 106.

As described above, and with reference to FIGS. 4 and 5, each outer crown 130, 132, and each mid-crown 134, 140 is a bend or turn. Thus, each outer crown 130, 132, and each mid-crown 134, 140 includes a first extrados crown end 154 where the outer surface of the outer crown 130, 132 or mid-crown 134, 140 begins/ends and the corresponding strut ends/begins and a second extrados crown end 156 wherein the outer surface of the crown ends/begins and the corresponding strut begins/ends. These extrados crown ends 154, 156 are indicated by dots on the outer surface of the wire 104 in FIG. 6. Similarly, each outer crown 130, 132, and each mid-crown 134, 140 includes a first intrados crown end 155 where the inner surface of the outer crown 130, 132 or mid-crown 134, 140 begins/ends and the corresponding strut ends/begins and a second intrados crown end 157 wherein the inner surface of the crown ends/begins and the corresponding strut begins/ends. These intrados crown ends 155, 157 are indicated by dots on the inner surface of the wire 104 in FIG. 6. For a selected outer crown or mid-crown, the radius of curvature of the intrados and the extrados of the crown define a crown center. Thus, for each wave of the waveform 106, the first outer crown 130 includes a first outer crown center 146, the first mid-crown 134 includes a first mid-crown center 148, the second outer crown 132 includes a second outer crown center 150, and the second mid-crown 140 includes a second mid-crown center 152.

The waveform 106 also includes a mid-crown wavelength distance MCD, which is defined by the perpendicular distance from the mid-crown center of a mid-crown to the crown center of the next outer crown in the waveform 104. Thus, in the example of the continuous wire stent 100 as shown in FIG. 6, the mid-crown wavelength distance MCD is the perpendicular distance from the first mid-crown center 148 to the second outer crown center 150. In embodiments hereof, the mid-crown wavelength distance is in the range of greater than 0 to a maximum value where the edge of the outer surface of a mid-crown touches the inside surface of the mid-crown or strut above it. In some embodiments, with a 6.5, 8.5 or 9.5 crown per wrap stent the mid-crown wavelength distance is in the range of 0.03 mm to 0.6 mm. The mid-crown wavelength distance MCD may also be expressed as a ratio or percentage. The mid-crown wavelength ratio is the mid-crown wavelength distance MCD divided by the maximum value where the edge of the outer surface of the outer surface of a mid-crown touches the inside surface of the mid-crown or strut above it. In embodiments, the mid-crown wavelength ratio may be between 10% and 90%, more preferably between 15% and 70%, and more preferably between 30% and 60%.

Referring to FIG. 4, the stent 100 also includes a plurality of connections 118 that are configured to connect selected outer crowns of 130, 132 of a band 108 with selected outer crowns 132, 130 of an adjacent band 108. The connections 118 may be created, for example and not by way of limitation, by fusing, welding, or soldering the selected outer crowns together. As used herein, "welding" and "soldering" are defined as heating an additional material that is separate from the selected outer crowns and applying the heated additional material to the selected outer crowns so that when the additional material cools, the selected outer crowns are welded or soldered together. Further, in the embodiment shown in FIG. 4, adjacent connections along the helical path of the bands 108 are spaced five waves apart from each other. Areas between adjacent connections 118 along the helical path of the waveform 106 in the central portion 110 are repeating body units 160. FIG. 4 shows one repeating body unit 160 highlighted. In an embodiment, the entire central portion 110 consists of repeating body units 160. In other embodiments, the repeating body unit may be defined more or fewer than five waves of the waveform 106. Using repeating body units for the central portion 110 of the continuous wire stent 100 enables the continuous wire stent 100 to be easily varied in length. In particular, the wire 104 formed into the waveform 106 may include enough repeating body units for a multiple of continuous wire stents. Depending on the desired length of the continuous wire stent 100, the wire 104 may be cut with more or less repeating body units. Therefore, instead of a waveform of a particular length made for each length stent, the wire 104 may be bent into one waveform and then be cut for different stent lengths. Further, in other embodiments, the central portion 110 may include different repeating body units such that the entire central portion does not consist of the same repeating body unit.

The continuous wire stent 100 of FIGS. 1-6 including a mid-crown between each adjacent first and second outer crowns provides several benefits. For example, and not by way of limitation, utilizing shorter struts due to the addition of a mid-crown provides a higher radial strength. Also, the mid-crowns nest within adjacent mid-crowns, thereby enabling the use of more wire material for the same diameter stent in the radially compressed configuration. Using additional wire material provides for more coverage of the stent.

The number of bands 108 in the central portion 110 and the central helical angle α may be determined by the particular specifications of the stent 100, such as the desired unexpanded and expanded diameters and the desired length of the stent 100, as well as the size (e.g., diameter) and particular material of the wire 104. The illustrated embodiments are not intended to be limiting in any way.

Figure 7:
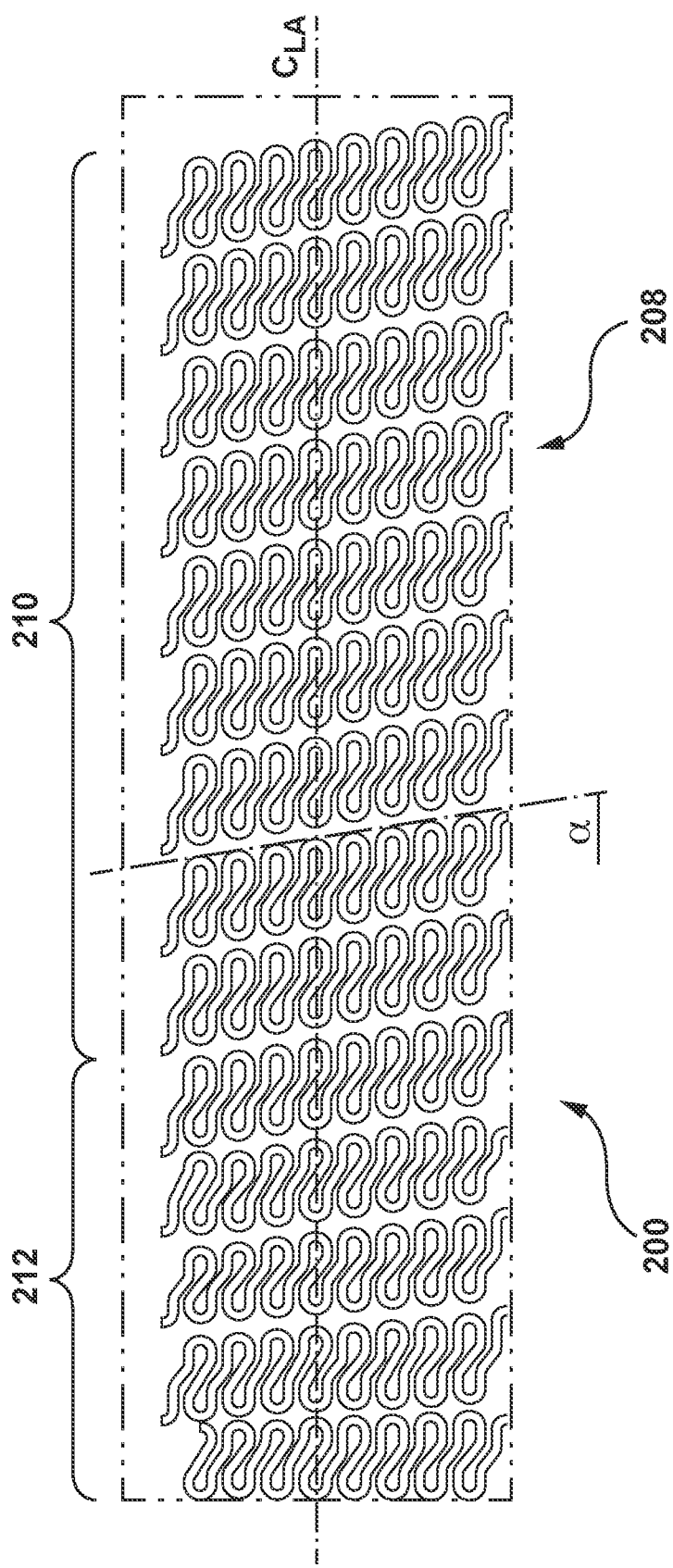
FIG. 7 is a flat layout view of a continuous wire stent according to another embodiment hereof.
Figure 8:
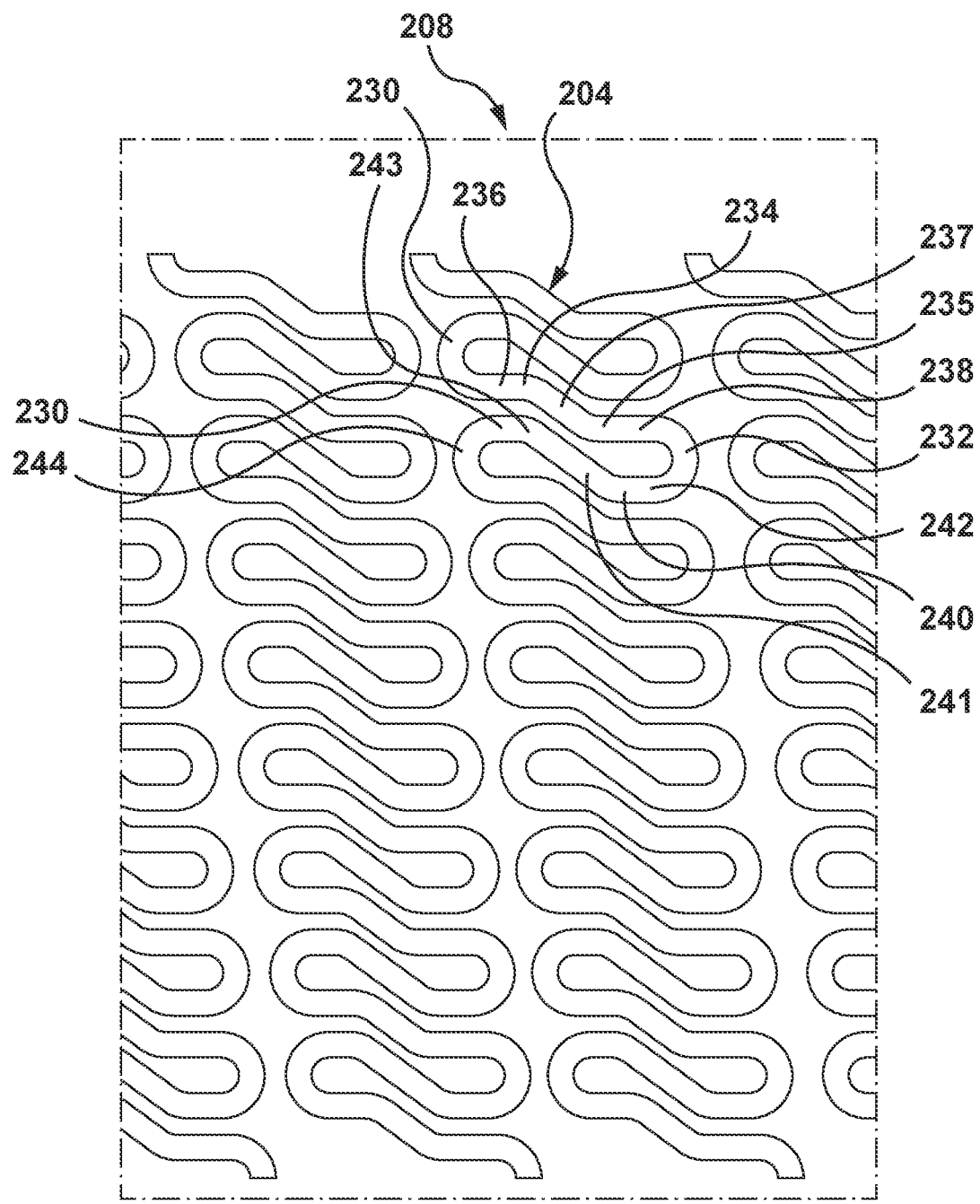
FIG. 8 is an enlarged view of a portion of the continuous wire stent of FIG. 7.
Figure 9:
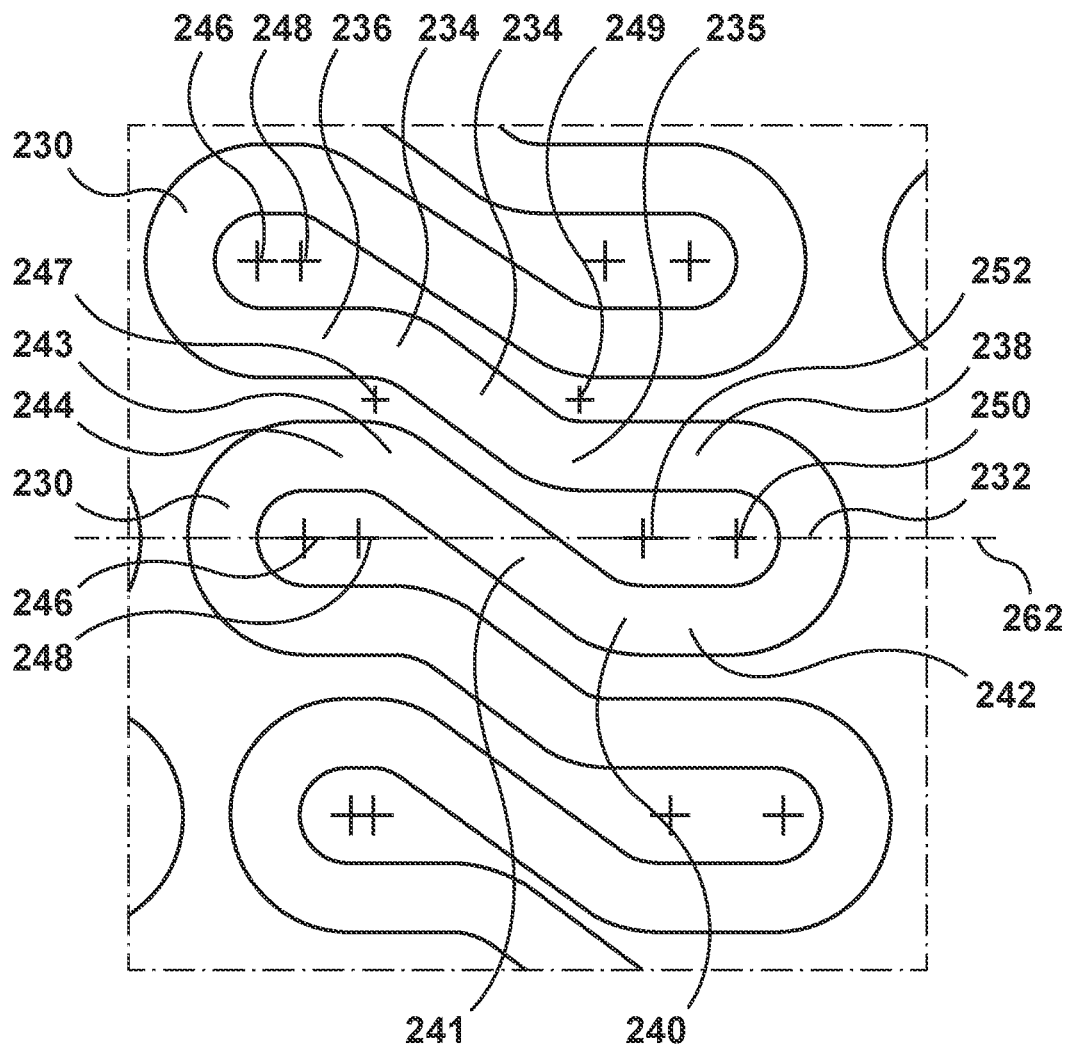
FIG. 9 is an enlarged view of a portion of the continuous wire stent of FIG. 7.

FIGS. 7-9 show a continuous wire stent 200 according to another embodiment hereof. FIG. 7 shows a flat layout of a portion of the continuous wire stent 200. Although the flat layout of the continuous wire stent 200 is shown in FIGS. 7-9, the continuous wire stent 200 is a generally tubular, open-ended structure that defines a lumen therethrough, as shown in FIGS. 1-2 for the continuous wire stent 100. The continuous wire stent 200 includes a radially compressed configuration for delivery to the affected site of a blood vessel, similar to as shown in FIG. 1, and a radially expanded configuration when deployed, similar to as shown in FIG. 2. The continuous wire stent 200 may be self-expanding or balloon expandable. The continuous wire stent 200 may be formed from a wire 204 formed into a waveform 206 and then helically wrapped (such as around a mandrel) to form the continuous wire stent 200. Other steps in processing the wire 204 and/or the continuous wire stent 200 may also be included. For example, and not by way of limitation, the wire 204 may be swaged prior to or after forming the wire 204 into the waveform 206. Swaging the wire 204 reduces the overall cross-section or diameter of the wire 204. Other steps such as connections between adjacent bands in the wrapped waveform, as explained in more detail below, polishing and other finishing steps may also be used in forming the continuous wire stent 204. The continuous wire stent 200 includes a first end 209 and a second end (not shown).

The wire 204 is a continuous element or strand that is bent into the waveform 206, and is wrapped into a helix having a plurality of windings, turns, or bands 208 that form a hollow cylindrical shape. The bands 208 are generally angled with respect to a central longitudinal axis CLA of the continuous wire stent 200 such that the bands or windings 208 are not perpendicular to the central longitudinal axis CLA. In particular, the bands 208 of the central portion 210 are disposed at an angle α between 60 and 85 degrees relative to the central longitudinal axis CLA, and preferably between 70 and 85 degrees. FIG. 7 shows the continuous wire stent 200 with a central portion 210 and a first end portion 212 disposed to a first side of the central portion 210. While not shown in FIG. 7, the continuous wire stent 200 may also include a second end portion disposed to a second side of the central portion 210 opposite the first end portion 212, similar to the second end portion 114 shown in FIG. 4. The first end portion 212 and the second end portion (not shown) may be included such that the ends of the continuous wire stent 200 are substantially orthogonal to the central longitudinal axis CLA of the continuous wire stent 200, as explained above and in U.S. Pat. No. 9,060,889, assigned to Medtronic Vascular, Inc., which is incorporated by reference herein in its entirety. Further, other ways to make the ends of the continuous wire stent 200 substantially orthogonal to the central longitudinal axis may be used. Accordingly, details regarding the first end portion 212 and the second end portion (not shown) will not be repeated with respect to the continuous wire stent 200.

In the embodiment of FIGS. 7-9, the waveform 206 of the continuous wire stent 200 includes two mid-crowns between each outer crown. Therefore, as best seen in FIGS. 8-9, each wave of the waveform 206 in the central portion 210 includes a repeating series of a first outer bend or crown 230, a second outer bend or crown 232, a first mid-bend or mid-crown 234 disposed between the first outer crown 230 and a second mid-crown 235, with the second mid-crown 235 disposed between the first mid-crown 234 and the second outer crown 232. The inner curve or intrados of the first outer crown 230 faces the inner curve or intrados of the second outer crown 232 such that the first outer crown 230 turns the wave towards the second outer crown 232 and the second outer crown 232 turns the wave towards the first outer crown 230. A first strut 236 connects the first outer crown 230 to the first mid-crown 234, a second strut 237 connects the first mid-crown 234 to the second mid-crown 235, and a third strut 238 connects the second mid-crown 235 to the second outer crown 232. A third mid-crown 240 is disposed between the second outer crown 232 and a fourth mid-crown 243, the fourth mid-crown 243 being disposed between the third mid-crown 240 and the first outer crown 230 in the next wave of the waveform 206. A fourth strut 242 connects the second outer crown 232 to the third mid-crown 240, a fifth strut 241 connects the third mid-crown 240 to the fourth mid-crown 243, and a sixth strut 244 connects fourth mid-crown 243 to the first outer crown 230 in the next wave of the waveform 206. Thus, a complete wave of the waveform 206 in a particular order starting from one of the first outer crowns 230 is the first outer crown 230, the first strut 236, the first mid-crown 234, the second strut 237, the second mid-crown 235, the third strut 238, the second outer crown 232 turning the wave in a generally opposite direction, the fourth strut 242, the third mid-crown 240, the fifth strut 241, the fourth mid-crown 243, and the sixth strut 244 connecting to another first crown 230 in the next wave of the waveform 206.

As described above with respect to the continuous wire stent 100, each outer crown and each mid-crown is a bend or turn that includes a center defined by the radius of curvature of the intrados and the extrados of the crown/mid-crown. Thus, in the embodiment of FIGS. 7-9 and shown in FIG. 9, for each wave of the waveform 206 of the continuous wire stent 200, the first outer crown 230 includes a first outer crown center 246, the first mid-crown 234 includes a first mid-crown center 247, the second mid-crown 235 includes a second mid-crown center 249, the second outer crown 232 includes a second outer crown center 250, the third mid-crown 240 includes a third mid-crown center 252, and the fourth mid-crown 243 includes fourth mid-crown center 248. The crown centers in FIGS. 7-9 are indicated by "plus" signs or "cross-hairs". In the embodiment of FIGS. 7-9, each first outer crown center 246 is co-linear with a fourth mid-crown center 248, a third mid-crown center 252, and a second outer crown center 250 on a line 262 that is parallel to the central longitudinal axis CLA of the continuous wire stent 200. Thus, the crowns are "longitudinally oriented".

The continuous wire stent 200 of FIGS. 7-9 including two mid-crowns between each adjacent first and second outer crowns provides several benefits. For example, and not by way of limitation, utilizing shorter struts due to the additional mid-crowns provides a higher radial strength. Also, the mid-crowns nest within adjacent mid-crowns, thereby enabling the use of more wire material for the same diameter stent in the radially compressed configuration. Using additional wire material provides for more coverage of the stent.

Although not shown in FIGS. 7-9, the continuous wire stent 200 may also include a plurality of connections configured to connect selected outer crowns 230, 232 of a band 208 with selected outer crowns 232, 230 of an adjacent band 208, such as the connections 118 described with respect to the continuous wire stent 100. The connections may be created, for example and not by way of limitation, by fusing, welding, or soldering the selected outer crowns together. As used herein, "welding" and "soldering" are defined as heating an additional material that is separate from the selected outer crowns and applying the heated additional material to the selected outer crowns so that when the additional material cools, the selected outer crowns are welded or soldered together. Further, adjacent connections along the helical path of the bands 208 may be spaced apart by a selected quantity of waves (such as five waves in the embodiment of FIGS. 1-6). Areas between adjacent connections along the helical path of the waveform 206 in the central portion 210 are repeating body units.

The continuous wire stent 200 shown in FIG. 7 includes nine bands 208 in the central portion 210 thereof. However, the quantity of bands 208 in the central portion 210 and other factors such as the central helical angle may be determined by the particular specifications of the continuous wire stent 200, such as the desired unexpanded and expanded diameters and the desired length of the stent 200, as well as the size (e.g., diameter) and particular material of the wire 204. The illustrated embodiments are not intended to be limiting in any way.

Figure 10:
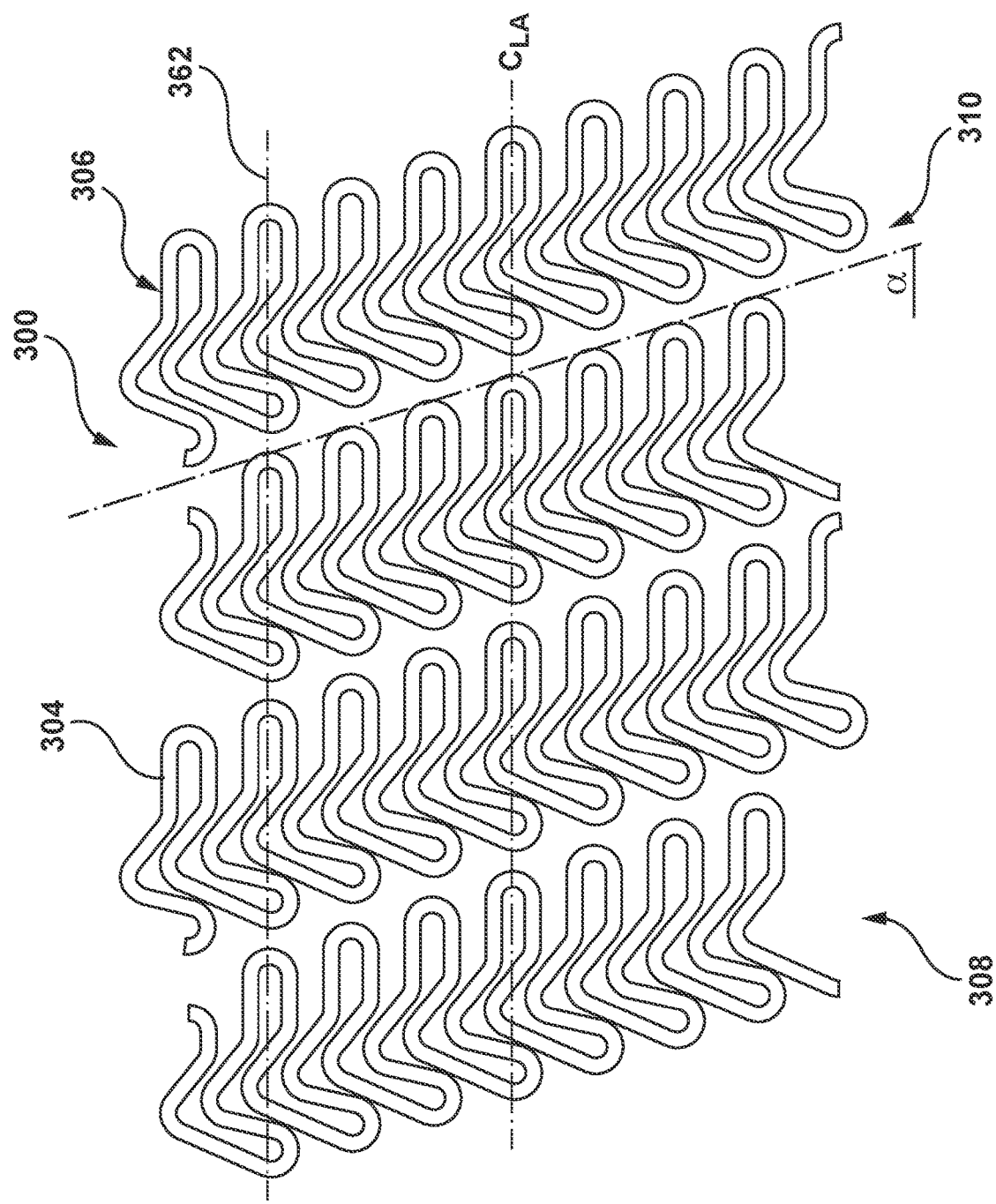
FIG. 10 is flat layout view of a portion of a continuous wire stent according to another embodiment hereof.
Figure 11:
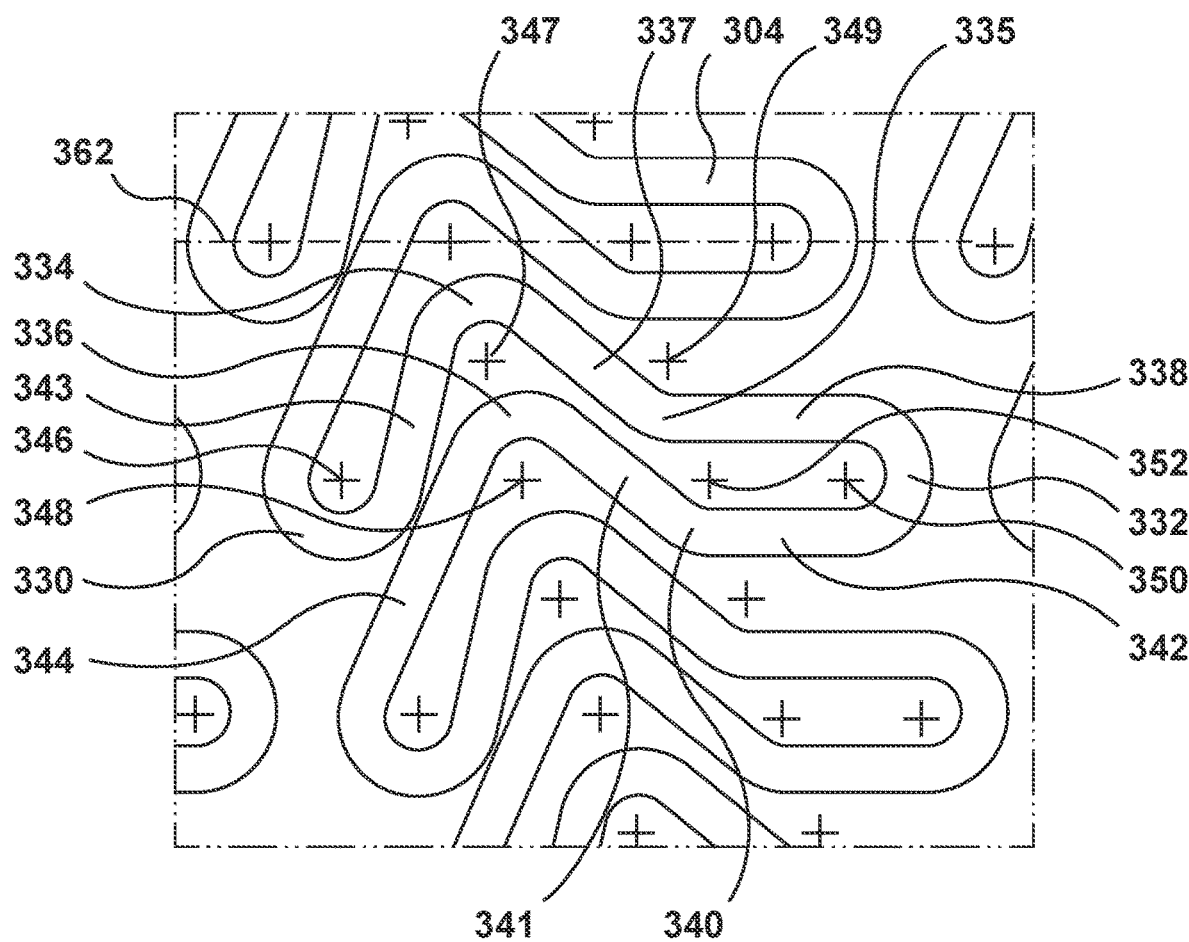
FIG. 11 is an enlarged view of a portion of the continuous wire stent of FIG. 10.

FIGS. 10-11 show a portion of a continuous wire stent 300 according to another embodiment hereof. FIG. 10 shows flat layout of a central portion 310 of the continuous wire stent 300. Although the flat layout of the continuous wire stent 300 is shown in FIGS. 10-11, the continuous wire stent 300 is a generally tubular, open-ended structure that defines a lumen therethrough, as shown in FIGS. 1-2 for the continuous wire stent 100. The continuous wire stent 300 includes a radially compressed configuration for delivery to the affected site of a blood vessel, similar to as shown in FIG. 1, and a radially expanded configuration when deployed, similar to as shown in FIG. 2. The continuous wire stent 300 may be self-expanding or balloon expandable. The continuous wire stent 300 is formed from a wire 304 formed into a waveform 306 and then helically wrapped (such as around a mandrel) to form the continuous wire stent 300. Other steps in processing the wire 304 and/or the continuous wire stent 300 may also be included. For example, and not by way of limitation, the wire 304 may be swaged prior to or after forming the wire 304 into the waveform 306. Swaging the wire 304 reduces the overall cross-section or diameter of the wire 304. Other steps such as connections between adjacent bands in the wrapped waveform, as explained in more detail below, polishing and other finishing steps may also be used in forming the continuous wire stent 304.

The wire 304 is a continuous element or strand that is bent into the waveform 306, and is wrapped into a helix having a plurality of windings, turns, or bands 308 that form a hollow cylindrical shape of the overall continuous wire stent 300. FIG. 10 shows the central portion 310 the continuous wire stent 300. The bands 308 are generally angled with respect to a central longitudinal axis CLA of the continuous wire stent 300 such that the bands or windings 308 are not perpendicular to the central longitudinal axis CLA. In particular, the bands 308 of the central portion 310 are disposed at an angle α between 60 and 85 degrees relative to the central longitudinal axis CLA, and preferably between 70 and 85 degrees. As explained above with respect to the embodiment of FIGS. 1-6, the continuous wire stent 300 may also include a first end portion (not shown in FIG. 10) disposed to a first side of the central portion 310 and a second end portion (not shown in FIG. 10) disposed to a second side of the central portion 310 opposite the first end portion. The first and second end portions (not shown) may be included such that the ends of the continuous wire stent 300 are substantially orthogonal to the central longitudinal axis CLA of the continuous wire stent 300, as explained above with respect to the continuous wire stent 100 and in U.S. Pat. No. 9,060,889, assigned to Medtronic Vascular, Inc., which is incorporated by reference herein in its entirety. Other ways to make the ends of the continuous wire stent 300 substantially orthogonal to the central longitudinal axis CLA may also be used. Accordingly, details regarding the first and second end portions will not be repeated with respect to the continuous wire stent 300. The first and second end portions of the continuous wire stent 300 may be similar to those described above and in the '889 patent, except with the waveform 306 of the continuous wire stent 300.

In the embodiment of FIGS. 10-11, the waveform 306 of the continuous wire stent 300 includes two mid-crowns between each outer crown. Therefore, as best seen in FIG. 11, each wave of the waveform 306 in the central portion 310 includes a repeating series of a first outer bend or crown 330, a second outer bend or crown 332, a first mid-bend or mid-crown 334 disposed between the first outer crown 330 and a second mid-crown 335, with the second mid-crown 335 being disposed between the first mid-crown 334 and the second outer crown 332. The inner curve or intrados of the first outer crown 330 faces the inner curve or intrados of the second outer crown 332 such that the first outer crown 330 turns the wave towards the second outer crown 332 and the second outer crown 332 turns the wave towards the first outer crown 330. A first strut 336 connects the first outer crown 330 to the first mid-crown 334, a second strut 337 connects the first mid-crown 334 to the second mid-crown 335, and a third strut 338 connects the second mid-crown 335 to the second outer crown 332. A third mid-crown 340 is disposed between the second outer crown 332 and a fourth mid-crown 343, the fourth mid-crown 343 being disposed between the third mid-crown 340 and the first outer crown 330 in the next wave of the waveform 306. A fourth strut 342 connects the second outer crown 332 to the third mid-crown 340, a fifth strut 341 connects the third mid-crown 340 to the fourth mid-crown 343, and a sixth strut 344 connects fourth mid-crown 343 to the first outer crown 330 in the next wave of the waveform 306. Thus, a complete wave of the waveform 306 in a particular order starting from one of the first outer crowns 330 is the first outer crown 330, the first strut 336, the first mid-crown 334, the second strut 337, the second mid-crown 335, the third strut 338, the second outer crown 332 turning the wave in a generally opposite direction, the fourth strut 342, the third mid-crown 340, the fifth strut 341, the fourth mid-crown 343, and the sixth strut 344 connecting to another first crown 330 in the next wave of the waveform 306.

As described above with respect to the continuous wire stent 100, each outer crown and each mid-crown is a bend or turn that includes a center defined by the radius of curvature of the intrados and the extrados of the crown/mid-crown. Thus, in the embodiment of FIGS. 10-11, as shown in FIG. 11, for each wave of the waveform 306 of the continuous wire stent 300, the first outer crown 330 includes a first outer crown center 346, the first mid-crown 334 includes a first mid-crown center 347, the second mid-crown 335 includes a second mid-crown center 349, the second outer crown 332 includes a second outer crown center 350, the third mid-crown 340 includes a third mid-crown center 352, and the fourth mid-crown 343 includes a fourth mid-crown center 348. The crown centers in FIGS. 10-11 are indicated by "plus" signs or "cross-hairs". In the embodiment of FIGS. 10-11, each first outer crown center 346 is co-linear with a fourth mid-crown center 348, a third mid-crown center 352, and a second outer crown center 350 on a line 362 that is parallel to the central longitudinal axis CLA of the continuous wire stent 300. Thus, the crowns are "longitudinally oriented". However, although the same types of crown centers are aligned in the continuous wire stent 300 as described above with respect to the continuous wire stent 200, the stents differ in that the first outer crown center 346 that is aligned with the fourth mid-crown center 348 is not associated with the first outer crown 330 that is connected to the fourth mid-crown 343 by the sixth strut 344, as in the embodiment of FIGS. 7-9. Instead, the first outer crown 330 associated with the first outer crown center 346 that is aligned with the fourth mid-crown center 348 is connected to the fourth mid-crown 343 by the first strut, the first mid-crown, the second strut, the second mid-crown, the third strut, the second outer crown, the fourth strut, the third mid-crown, and the fifth strut. Thus, it could be stated that the first outer crown center 346 that is aligned with the fourth mid-crown center 348 is the first outer crown center 346 associated with the first outer crown 330 that starts a wave and the fourth mid-crown center 348 is associated with the fourth mid-crown 343 associated with end of that wave. To the contrary, in the embodiment of FIGS. 7-9 the fourth mid-crown center 248 that is aligned with the first outer crown center 246 is associated with the fourth mid-crown 243 to end a wave and the first outer crown center 246 is associated with the first outer crown 230 to start the next wave.

The continuous wire stent 300 of FIGS. 10-11 including two mid-crowns between each adjacent first and second outer crowns provides several benefits. For example, and not by way of limitation, utilizing shorter struts due to the additional mid-crowns provides a higher radial strength. Also, the mid-crowns nest within adjacent mid-crowns, thereby enabling the use of more wire material for the same diameter stent in the radially compressed configuration. Using additional wire material provides for more coverage of the stent.

Although not shown in FIGS. 10-11, the continuous wire stent 300 may also include a plurality of connections configured to connect selected outer crowns 330, 332 of a band 308 with selected outer crowns 332, 330 of an adjacent band 308, such as the connections 118 described with respect to the continuous wire stent 100. The connections may be created, for example and not by way of limitation, by fusing, welding, or soldering the selected outer crowns together. As used herein, "welding" and "soldering" are defined as heating an additional material that is separate from the selected outer crowns and applying the heated additional material to the selected outer crowns so that when the additional material cools, the selected outer crowns are welded or soldered together. Further, adjacent connections along the helical path of the bands 308 may be spaced apart by a selected quantity of waves (such as five waves in the embodiment of FIGS. 1-6). Areas between adjacent connections along the helical path of the waveform 306 in the central portion 310 are repeating body units.

The continuous wire stent 300 may include any suitable quantity of bands 308 in the central portion 310 thereof, depending on particular specifications of the continuous wire stent 300, such as, but not limited to, the desired unexpanded and expanded diameters and the desired length of the stent 300, as well as the size (e.g., diameter) and particular material of the wire 304. The illustrated embodiments are not intended to be limiting in any way.

Figure 12:
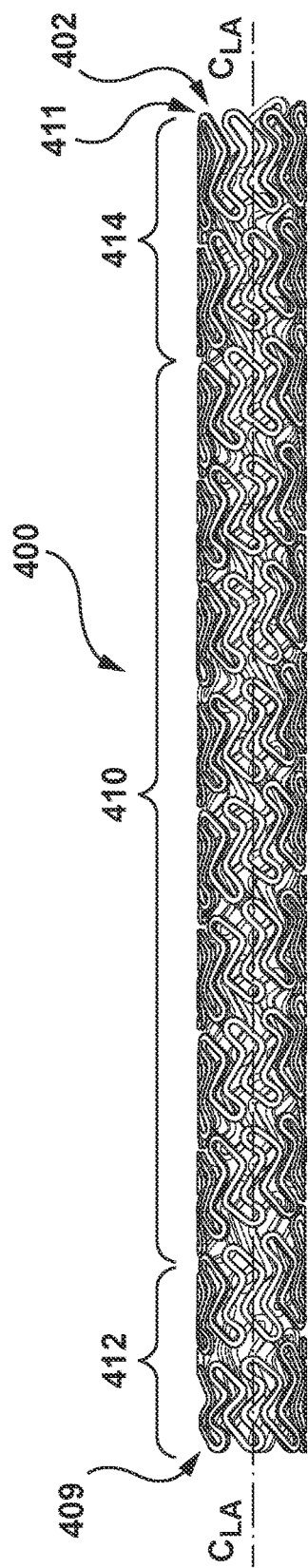
FIG. 12 is a perspective view of a continuous wire stent according to another embodiment hereof.
Figure 13:
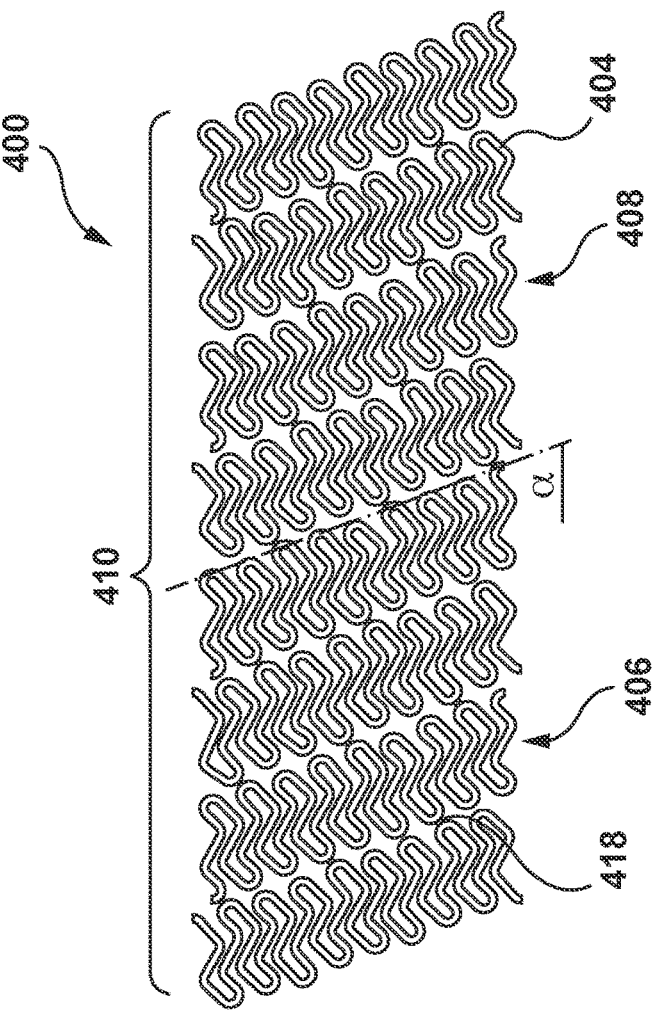
FIG. 13 is a flat layout view of the continuous wire stent of FIG. 12.
Figure 14:
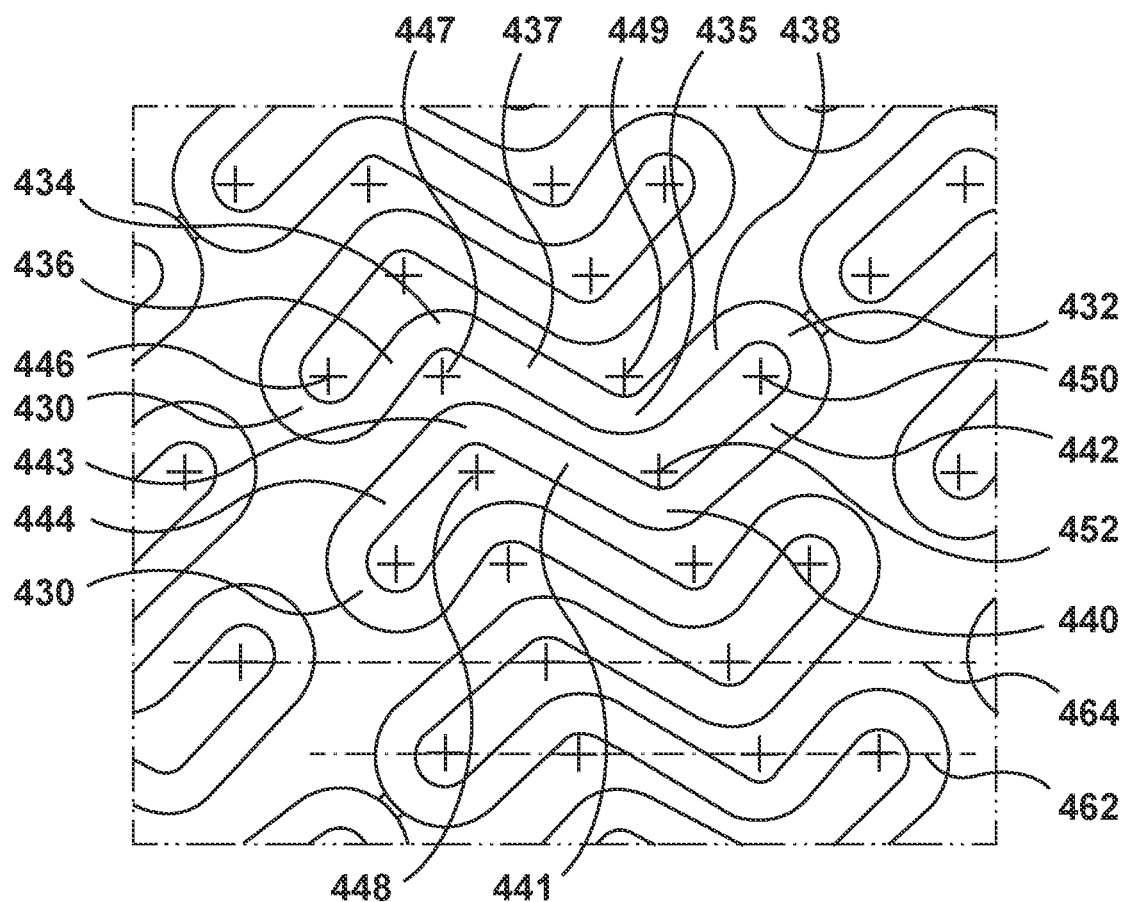
FIG. 14 is an enlarged view of a portion of the continuous wire stent of FIG. 13.

FIGS. 12-14 show a continuous wire stent 400 according to another embodiment hereof. FIG. 12 is a perspective view of the continuous wire stent 400 in a radially compressed configuration for delivery to the affected site of a blood vessel. The continuous wire stent 400 also includes a radially expanded configuration when deployed, similar to the continuous wire stent 100 shown in FIG. 2. The continuous wire stent 400 is a generally tubular, open-ended structure including a first end 409 and a second end 411, and defining a lumen 402 therethrough. The continuous wire stent 400 may be self-expanding or balloon expandable. The continuous wire stent 400 is formed from a wire 404 formed into a waveform 406 and then helically wrapped (such as around a mandrel) to form the continuous wire stent 400. Other steps in processing the wire 404 and/or the continuous wire stent 400 may also be included. For example, and not by way of limitation, the wire 404 may be swaged prior to or after forming the wire 304 into the waveform 406. Swaging the wire 404 reduces the overall cross-section or diameter of the wire 404. Other steps such as connections between adjacent bands in the wrapped waveform, as explained in more detail below, polishing and other finishing steps may also be used in forming the continuous wire stent 404.

The wire 404 is a continuous element or strand that is bent into the waveform 406, and is wrapped into a helix having a plurality of windings, turns, or bands 408 that form a hollow cylindrical shape of the overall continuous wire stent 400. In the embodiment shown in FIG. 12, the continuous wire stent 400 includes twelve bands 408. However, this is not limiting and the continuous wire stent 400 may include more or fewer bands 408. In the embodiment of FIG. 12, the bands 408 form three portions of the continuous wire stent 400, a central portion 410, a first end portion 412 disposed to a first side of the central portion 410, and a second end portion 414 disposed to a second side of the central portion 410 opposite the first end portion 412. The bands 408 are generally angled with respect to a central longitudinal axis CLA of the continuous wire stent 400 such that the bands or windings 408 are not perpendicular to the central longitudinal axis CLA. In particular, the bands 408 of the central portion 410 are disposed at an angle $\alpha$ between 60 and 85 degrees relative to the central longitudinal axis CLA, and preferably between 70 and 85 degrees.

In an embodiment, the continuous wire stent 400 may have ends 409, 411 that are substantially orthogonal to the central longitudinal axis CLA. The ends 409, 411 may be made substantially orthogonal to the central longitudinal axis CLA of the continuous wire stent 400 as explained above with respect to the continuous wire stent 100 and in U.S. Pat. No. 9,060,889, assigned to Medtronic Vascular, Inc., which is incorporated by reference herein in its entirety. Other ways to make the ends of the continuous wire stent 400 substantially orthogonal to the central longitudinal axis CLA may also be used. Accordingly, details regarding the first and second end portions 412 and 414 will not be repeated with respect to the continuous wire stent 400. The first and second end portions 412, 414 of the continuous wire stent 400 may be similar to those described above and in the '889 patent, except with the waveform 406 of the continuous wire stent 400.

As best shown in FIGS. 13-14, the waveform 406 for the central portion 410 includes two mid-crowns between each outer crown. Therefore, each wave of the waveform 406 in the central portion 410 includes a repeating series of a first outer bend or crown 430, a second outer bend or crown 432, a first mid-bend or mid-crown 434 disposed between the first outer crown 430 and a second mid-crown 435, with the second mid-crown 435 being disposed between the first mid-crown 434 and the second outer crown 432. The inner curve or intrados of the first outer crown 430 faces the inner curve or intrados of the second outer crown 432 such that the first outer crown 430 turns the wave towards the second outer crown 432 and the second outer crown 432 turns the wave towards the first outer crown 430. A first strut 436 connects the first outer crown 430 to the first mid-crown 434, a second strut 437 connects the first mid-crown 434 to the second mid-crown 435, and a third strut 438 connects the second mid-crown 435 to the second outer crown 432. A third mid-crown 440 is disposed between the second outer crown 432 and a fourth mid-crown 443, the fourth mid-crown 443 being disposed between the third mid-crown 440 and the first outer crown 430 in the next wave of the waveform 406. A fourth strut 442 connects the second outer crown 432 to the third mid-crown 440, a fifth strut 441 connects the third mid-crown 440 to the fourth mid-crown 443, and a sixth strut 444 connects fourth mid-crown 443 to the first outer crown 430 in the next wave of the waveform 406. Thus, a complete wave of the waveform 406 in a particular order starting from one of the first outer crowns 430 is the first outer crown 430, the first strut 436, the first mid-crown 434, the second strut 437, the second mid-crown 435, the third strut 438, the second outer crown 432 turning the wave in a generally opposite direction, the fourth strut 442, the third mid-crown 440, the fifth strut 441, the fourth mid-crown 443, and the sixth strut 444 connecting to another first crown 430 in the next wave of the waveform 406.

As described above with respect to the continuous wire stent 100, each outer crown and each mid-crown is a bend or turn that includes a center defined by radius of curvature of the intrados and the extrados of the crown/mid-crown. Thus, in the embodiment of FIGS. 12-14, as shown in FIG. 14, for each wave of the waveform 406 of the continuous wire stent 400, in the radially compressed configuration, the first outer crown 430 includes a first outer crown center 446, the first mid-crown 434 includes a first mid-crown center 447, the second mid-crown 435 includes a second mid-crown center 449, the second outer crown 432 includes a second outer crown center 450, the third mid-crown 440 includes a third mid-crown center 452, and the fourth mid-crown 443 includes a fourth mid-crown center 448. The crown centers in FIG. 14 are indicated by "plus" signs or "cross-hairs". In the embodiment of FIGS. 12-14, each first outer crown center 446 is co-linear with the first mid-crown center 447, the second mid-crown center 452, and the second outer crown center 450 on a line 462 that is parallel to the central longitudinal axis CLA of the continuous wire stent 400. Further, the third mid-crown center 452 and the fourth mid-crown center 448 are co-linear on a line 464 that is parallel to the central longitudinal axis CLA of the continuous wire stent 400.

The continuous wire stent 400 of FIGS. 12-14 including two mid-crowns between each adjacent first and second outer crowns provides several benefits. For example, and not by way of limitation, utilizing shorter struts due to the additional mid-crowns provides a higher radial strength. Also, the mid-crowns nest within the mid-crowns of adjacent waves, thereby enabling the use of more wire material for the same diameter stent in the radially compressed configuration. Using additional wire material provides for more coverage of the stent. Further, for a particular amplitude of the waves of the waveform 406, the lockout diameter for the continuous wire stent 400 is greater than an equivalent stent without the mid-crowns. Further, the continuous wire stent 400 can achieve the same lockout diameter as an equivalent stent without the mid-crowns with a smaller amplitude of the waves of the waveform. A smaller amplitude in turn provides for shorter strut lengths, which increases radial strength.

Referring to FIG. 13, the stent 400 also includes a plurality of connections 418 that are configured to connect selected outer crowns of 430, 432 of a band 408 with selected outer crowns 432, 430 of an adjacent band 408. The connections 418 may be created, for example and not by way of limitation, by fusing, welding, or soldering the selected outer crowns together. As used herein, "welding" and "soldering" are defined as heating an additional material that is separate from the selected outer crowns and applying the heated additional material to the selected outer crowns so that when the additional material cools, the selected outer crowns are welded or soldered together. Further, in the embodiment shown in FIG. 13, adjacent connections along the helical path of the bands 408 are spaced three (3) waves apart from each other. Areas between adjacent connections 418 along the helical path of the waveform 406 in the central portion 410 are repeating body units 460. FIG. 13 shows one repeating body unit 460 highlighted. In an embodiment, the entire central portion 410 consists of repeating body units 460. However, in other embodiments, the repeating bod unit may be defined more or fewer than three (3) waves of the waveform 406. Further, in other embodiments, the central portion 410 may include different repeating body units such that the entire central portion does not consist of the same repeating body unit.

The number of bands 408 in the central portion 410 and the central helical angle α may be determined by the particular specifications of the stent 400, such as the desired unexpanded and expanded diameters and the desired length of the stent 400, as well as the size (e.g., diameter) and particular material of the wire 404. The illustrated embodiments are not intended to be limiting in any way.

The wire 104, 204, 304, 404 of any of the embodiments described above may be any material suitable for use as a stent. For example, and not by way of limitation, the wire 104, 204, 304, 404 may be stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the wire 104, 204, 304, 404 may be formed from a cobalt alloy, such as L605 or MP35N®, Nitinol (nickel-titanium shape memory alloy), ABI (palladium-silver alloy), Elgiloy® (cobalt-chromium-nickel alloy), molybdenum-rhemium alloys, and other materials suitable for use in a stent. It is also contemplated that the wire may be formed from two or more materials that are laminated together, such as tantalum that is laminated with MP35N®. The wire 104, 204, 304, 404 may also have concentric layers of different materials. For example, and not by way of limitation, the wire 104, 204, 304, 404 may be a drawn-filled tube with an outer layer of a cobalt-chromium alloy with a platinum-iridium core disposed within the cobalt-chromium alloy for enhanced radiopacity and visibility under fluoroscope. The aforementioned materials and laminations are intended to be examples and are not intended to be limiting in any way. Further, the cross-sectional shape of wire 104, 204, 304, 404 may be round, oblong, D-shaped, oval, or any other suitable shape.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A continuous wire stent including a radially compressed configuration and the radially expanded configuration, the continuous wire stent in the radially compressed configuration comprising:
    a wire bent into a waveform and spirally wrapped into a helix having a plurality of bands that form a hollow cylindrical shape, at least a portion of the helix including a plurality of repeating body units including a plurality of waves including
        a first outer crown including a first intrados and a first outer crown center,
        a second outer crown including a second intrados facing the first intrados and a second outer crown center,
        a first mid-crown disposed between the first outer crown and a second mid-crown, the second mid-crown being disposed between the first mid-crown and the second outer crown, the first mid-crown including a first mid-crown center and the second mid-crown including a second mid-crown center,
        a first strut connecting the first outer crown to the first mid-crown,
        a second strut connecting the first mid-crown to the second mid-crown,
        a third strut connecting the second mid-crown to the second outer crown,
        a third mid-crown disposed between the second outer crown and a fourth mid-crown, the fourth mid-crown being disposed between the third mid-crown and a next outer crown in a next wave of the waveform, the third mid-crown including a third mid-crown center and the fourth mid-crown including a fourth mid-crown center,
        a fourth strut connecting the second outer crown to the third mid-crown,
        a fifth strut connecting the third mid-crown to the fourth mid-crown, and
        a sixth strut connecting fourth mid-crown to the outer crown in the next wave of the waveform, the next outer crown including a next outer crown center,
    wherein in the radially compressed configuration, the second outer crown center, the third mid-crown center, the fourth mid-crown center, and the next outer crown center are co-linear on a line that is parallel to a central longitudinal axis of the continuous wire stent.

2. The continuous wire stent of claim 1, wherein the plurality of repeating body units are disposed in a central portion of the continuous wire stent.

3. The continuous wire stent of claim 2, wherein the helix in the central portion is wrapped at non-perpendicular angle with respect to a central longitudinal axis of the continuous wire stent.

4. The continuous wire stent of claim 3, wherein the non-perpendicular angle is between 60 and 85 degrees.

5. The continuous wire stent of claim 1, wherein the plurality of repeating body units are disposed in a central portion of the continuous wire stent.

6. The continuous wire stent of claim 5, wherein the continuous wire stent further comprises a first end portion disposed to a first side of the central portion and a second end portion disposed to a second side of the central portion opposite the first portion, wherein the first end portion and the second end portion are configured such that a first end of the continuous wire stent and a second end of the continuous wire stent are substantially orthogonal to a central longitudinal axis of the continuous wire stent.

7. The continuous wire stent of claim 6, wherein the helix in the central portion is wrapped at a first angle with respect to a central longitudinal axis of the continuous wire stent, and wherein the helix in the first end portion is wrapped at a second angle with respect to the central longitudinal axis of the continuous wire stent, the second angle being different than the first angle.

8. The continuous wire stent of claim 1, further comprising connections between adjacent bands of the helix, wherein each repeating body unit is defined between adjacent connections along the helix.

* * * * *